United States Patent
Bhatia et al.

(10) Patent No.: US 10,330,621 B1
(45) Date of Patent: Jun. 25, 2019

(54) ELECTROLYTE SENSOR AND METHOD AND PRODUCING THEREOF

(71) Applicant: Theos Medical Systems, Los Altos, CA (US)

(72) Inventors: Saket Bhatia, Santa Clara, CA (US); Ankush Bhatia, Vancouver (CA)

(73) Assignee: Theos Medical Systems, Inc., Santa Clara, CA (US)

( * ) Notice: Subject to any disclaimer, the term of this patent is extended or adjusted under 35 U.S.C. 154(b) by 0 days.

(21) Appl. No.: 15/638,339

(22) Filed: Jun. 29, 2017

Related U.S. Application Data

(63) Continuation of application No. 14/292,949, filed on Jun. 2, 2014, now Pat. No. 9,726,629, which is a continuation-in-part of application No. 12/946,853, filed on Nov. 15, 2010, now abandoned, which is a continuation of application No. 12/658,371, filed on Feb. 12, 2010, now abandoned.

(51) Int. Cl.
| | |
|---|---|
| *G01N 27/30* | (2006.01) |
| *G01N 27/07* | (2006.01) |
| *G01N 27/403* | (2006.01) |
| *G01N 27/327* | (2006.01) |
| G01N 33/493 | (2006.01) |
| A61B 5/00 | (2006.01) |
| A61B 5/20 | (2006.01) |

(52) U.S. Cl.
CPC ............ *G01N 27/07* (2013.01); *G01N 27/327* (2013.01); *G01N 27/403* (2013.01); *A61B 5/202* (2013.01); *A61B 5/6804* (2013.01); *A61B 5/6808* (2013.01); *G01N 33/493* (2013.01); *Y10T 29/49181* (2015.01)

(58) Field of Classification Search
CPC ............ G01N 27/327; G01N 27/3272; G01N 27/403; G01N 27/06; A61B 5/202; A61B 5/207; A61B 5/6804–5/6808
See application file for complete search history.

(56) References Cited

U.S. PATENT DOCUMENTS

| | | | |
|---|---|---|---|
| 9,726,629 B2 * | 8/2017 | Bhatia | G01N 27/07 |
| 2002/0142677 A1 * | 10/2002 | Hosaka | H01R 4/024 |
| | | | 439/874 |

OTHER PUBLICATIONS

Parker Chomerics product literature entitled "Extruded Nickel-Plated Graphite Filled Elastomers", published Dec. 2004. (Year: 2004).*

* cited by examiner

*Primary Examiner* — Alexander S Noguerola

(57) ABSTRACT

Provided is an electrolyte sensor that uses conductive elastomer electrodes. Examples of the intended analytes for sensor use include those found in urine, saliva, blood, feces, and spinal fluid, although other analytes exist for electrolyte detection. Conductive elastomer trace electrodes are separated by a channel or gap which can be bridged by an electrolyte and thereby complete an electrical circuit to an alarm or other circuitry. Channel or gap distances vary the level of electrical resistance associated with detecting certain analytes.

20 Claims, 21 Drawing Sheets

ELECTROLYTE SENSOR AND METHOD AND PRODUCING THEREOF

RELATED APPLICATIONS

This patent application is a Continuation application that claims the priority benefit of U.S. non-provisional patent application Ser. No. 14/292,949 filed on Jun. 2, 2014 and titled "An Electrolyte Sensor Using Conductive Elastomer," which is hereby incorporated by reference in its entirety.

FIELD

The present disclosure relates to the use of conductive elastomers in electronics. More specifically, the present disclosure relates to electrodes used in sensors. More specifically, the present disclosure relates to electrodes used in a sensor to detect electrolytes including, but not limited to, those present in urine, sweat, blood, feces, saliva and spinal fluid.

BACKGROUND

Existing fluid detection alarms can be attached to a user's clothes with a safety pin, magnet, or specialized clips. Not only are these approaches limiting in nature, they can create various inconveniences for the user. Even though attaching a fluid detection alarm to the user's clothes can ensure that it is close enough to be heard, the sound can be easily muffled if the user is covered with a blanket or some other covering. Besides, the user would be forced to sleep in one position to ensure that he/she is not sleeping on the fluid detection alarm. Additionally, safety pins and specialized clips can easily impair the comfort and convenience of the user, while magnets are often not strong enough to hold a fluid detection alarm.

The approaches described in this section could be pursued, but are not necessarily approaches that have been previously conceived. Therefore, unless otherwise indicated herein, the approaches described in this section are not prior art to the claims in this application and are not admitted to be prior art by inclusion in this section.

The use of conductive polymers and conductive elastomers is commonly known in the form of gaskets or seals due to their elasticity and conductivity. Some of the useful properties as a conductor include facile shape formation, corrosion resistance, and airtight contact interface. Use as a conductor is limited, however, because it is difficult to obtain as low a resistivity as in metals. Conductive elastomers are typically composed of silicone rubber that has had conductive carbon or metal particles introduced. The resistivity of the material changes with the conductive particle content.

The use of sensor electrodes attached electrically to an alarm unit for the purpose of treatment enuresis therapy is well known. Electrolytes present in urine enable completion of an alarm circuit by filling a channel or gap between electrodes and thereby indicating the occurrence of a micturition event. Most existing electrodes have either a set of parallel or else linear serpentine positive and negative electrode patterns wherein urine contacts both a positive and negative bare wire to complete the alarm circuit. The bare wire is made available for contact with urine through gaps in an insulator, whereby urine enters a positive and negative gap to contact a wire and complete a circuit.

Existing electrolyte sensors are limited to circuit completion along a single narrow gap between two conductive plastic zone halves, each half respectively in contact with one positive conductive element and one negative conductive element that extend into the sensor body from a terminal socket. This is disadvantageous because an electrolyte may be present in one of the plastic zone halves and never close the electric circuit wherein the entire sensor surface is comprised only of the two zone halves. The present disclosure is not limited in this way. Conductive elastomer positive and negative trace electrodes may be connected to respective wire lead terminals and the conductive elastomer trace electrodes may be in close proximity to each other throughout a sensor "trace pattern" so that an electrolyte can close the circuit by simultaneously touching any point along the surface of a positive and a negative trace electrode throughout the entire trace pattern which takes up the entire sensor surface. This is an important improvement given that a penis or other electrolyte source is unpredictable in electrolyte placement and the volume or amount of electrolyte required to close a circuit should be as low as possible and corresponding circuit completion as quick as possible for effective therapy where every moment counts in training the nervous system. Examples of sensor trace patterns are illustrated in FIGS. 2A-2K.

Another advantage over the existing solutions is the use of heat molding to attach the trace electrodes. Considerably larger and more robust than existing sensor films or printed circuits, the present heat molded elastomeric electrodes are able to withstand both being worn overnight by a user as well as degradation by caustic substances such as urine. Available wetness sensors detect leaks from catheter sites using exclusively a circuit printed onto a solid nonflexible support. Such a circuit would not withstand the caustic effect of urine combined with continuous overnight use by a wearer.

Sensors used to detect electrolytes present in things other than urine operate on the same principle of forming a conductive bridge between sensor electrodes, and the function of the completed circuit operates to contribute to different forms of therapy depending on what is being detected by the sensor, the upstream electronics, and which human system is being treated. Examples of additional purposes include detecting blood or spinal fluid leaking from catheter sites and sensing feces in a diaper. These examples are not exclusive from other uses but instead are meant to describe some of the utilities for the use of conductive elastomer in sensor electrodes and where it is illustrated that a conductive elastomer electrode is universally an improvement over the existing solutions for many reasons, but especially because electrolytes can contact any part of the surface of the robust conductive elastomer trace electrodes and result immediately in a current, whereas the existing solutions require additional time for electrolytes to come into contact with interspersed metal wire contact points or be of sufficient volume and directionality to connect plastic electrode zone halves.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Provided are an electrolyte sensor for detecting an analyte and a method for producing the electrolyte sensor.

In certain embodiments, the electrolyte sensor may include a flexible nonconductive silicone base portion and wire crimps attached to wire lead terminals. The wire crimps may be arranged on the flexible nonconductive silicone base portion. The electrolyte sensor may further include one or more positive and negative trace electrodes covering the wire crimps. The flexible nonconductive silicone base portion, the wire crimps, and the one or more positive and negative trace electrodes may be connected together by using heat molding and vulcanization. The flexible nonconductive silicone base portion may enable separation of the one or more positive and negative trace electrodes. The one or more positive and negative trace electrodes may include a conductive polymer and may be arranged in a pattern of proximity with respect to each other throughout a surface of the electrolyte sensor.

In certain embodiments, the wire lead terminals may be connected to respective positive and negative battery terminals.

In certain embodiments, the conductive polymer may be an elastomer.

In certain embodiments, the proximity between the one or more positive and negative trace electrodes may be sufficient to prevent conducting of an electric current between the one or more positive and negative trace electrodes.

In certain embodiments, the proximity may be formed by one or more channels or gaps of an uneven dimension.

In certain embodiments, the one or more positive and negative trace electrodes form islands throughout the surface, with the one or more channels or gaps separating the islands.

In certain embodiments, the one or more channels or gaps may be of sufficient size to allow analyte present in a solid, liquid, or gas to conduct electricity between the one or more positive and negative trace electrodes.

In certain embodiments, the one or more positive and negative trace electrodes may be separated by one or more bridges.

In certain embodiments, the flexible nonconductive silicone base portion may be of a sufficient rigidity to provide a distance between the one or more positive and negative trace electrodes.

In certain embodiments, the method for producing an electrolyte sensor for detecting an analyte may include providing a flexible nonconductive silicone base portion, one or more positive and negative trace electrodes, and wire crimps. The method may further include attaching the wire crimps to wire lead terminals and placing the wire crimps over the flexible nonconductive silicone base portion. The method may further include covering the wire crimps with the one or more positive and negative trace electrodes and connecting the flexible nonconductive silicone base portion, the wire crimps and the one or more positive and negative trace electrodes together using heat molding and vulcanization.

In certain embodiments, the method may further include fusing a single piece of a cable to the electrolyte sensor through a strain relief.

Other features and exemplary embodiments are described below.

BRIEF DESCRIPTION OF DRAWINGS

Embodiments are illustrated by way of example and not limitation in the figures of the accompanying drawings, in which like references indicate similar elements and in which.

DETAILED DESCRIPTION

Figure 1:
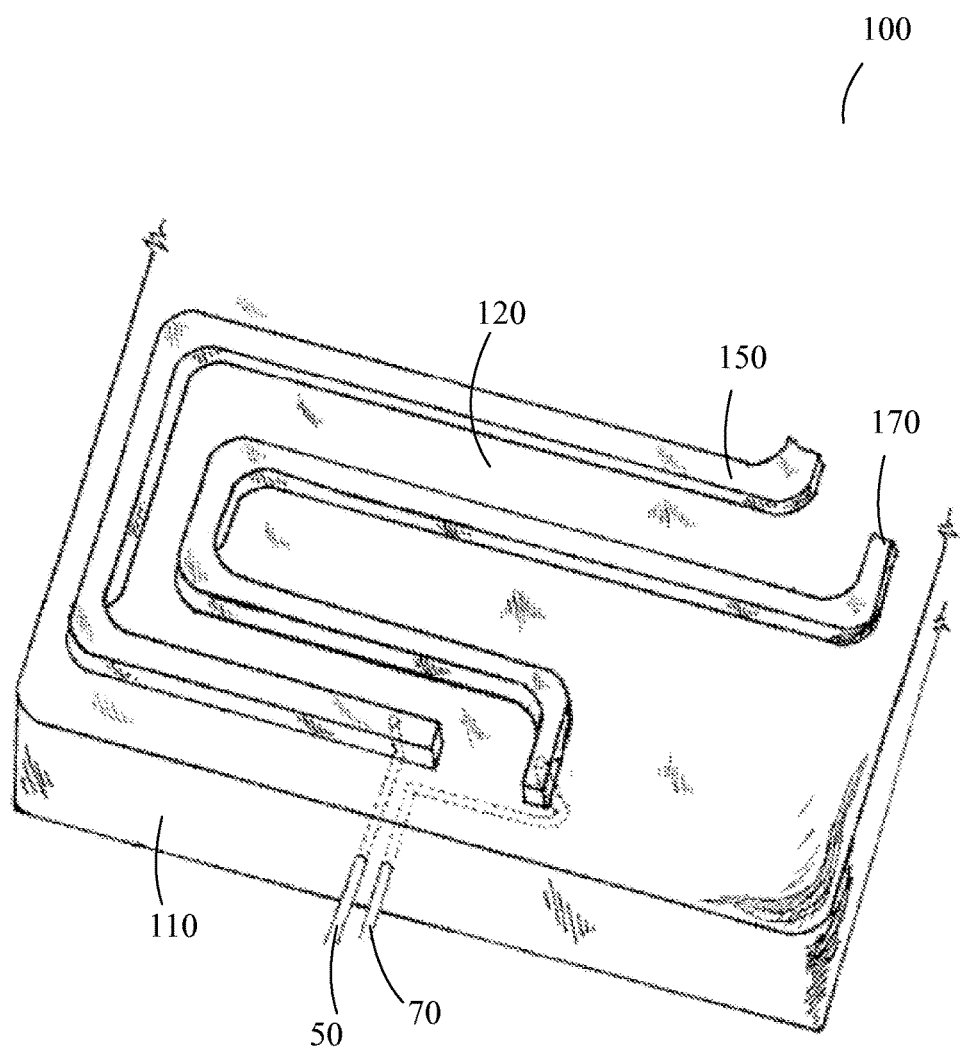
FIG. 1 is a perspective view illustrating the incoming wire lead terminals attached to a flexible nonconductive silicone base portion and the trace electrodes, in accordance with an example embodiment.
Figure 2A:
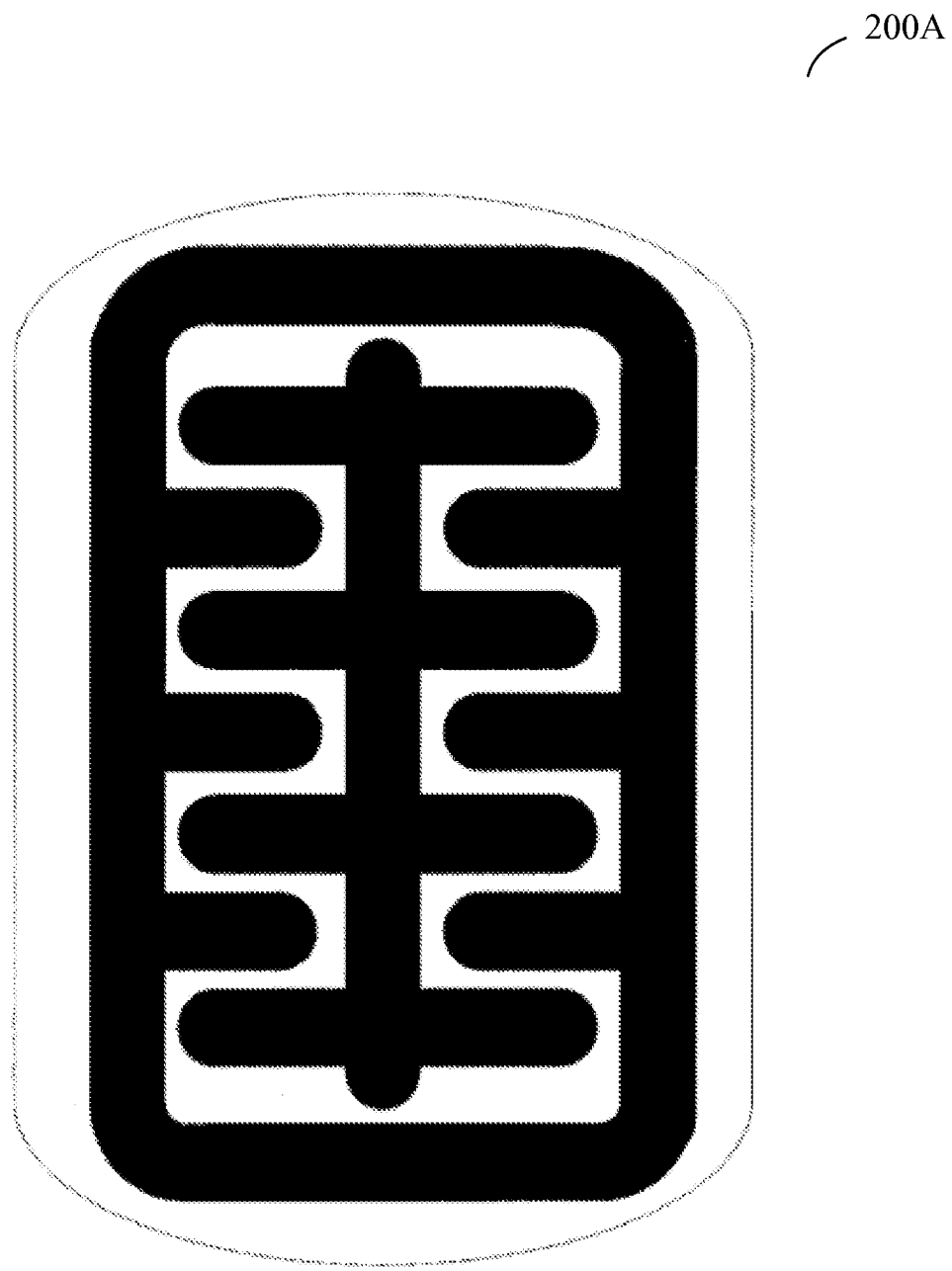
FIGS. 2A-K show various electrode trace patterns as patterns made available, in accordance with an example embodiment.
Figure 2B:
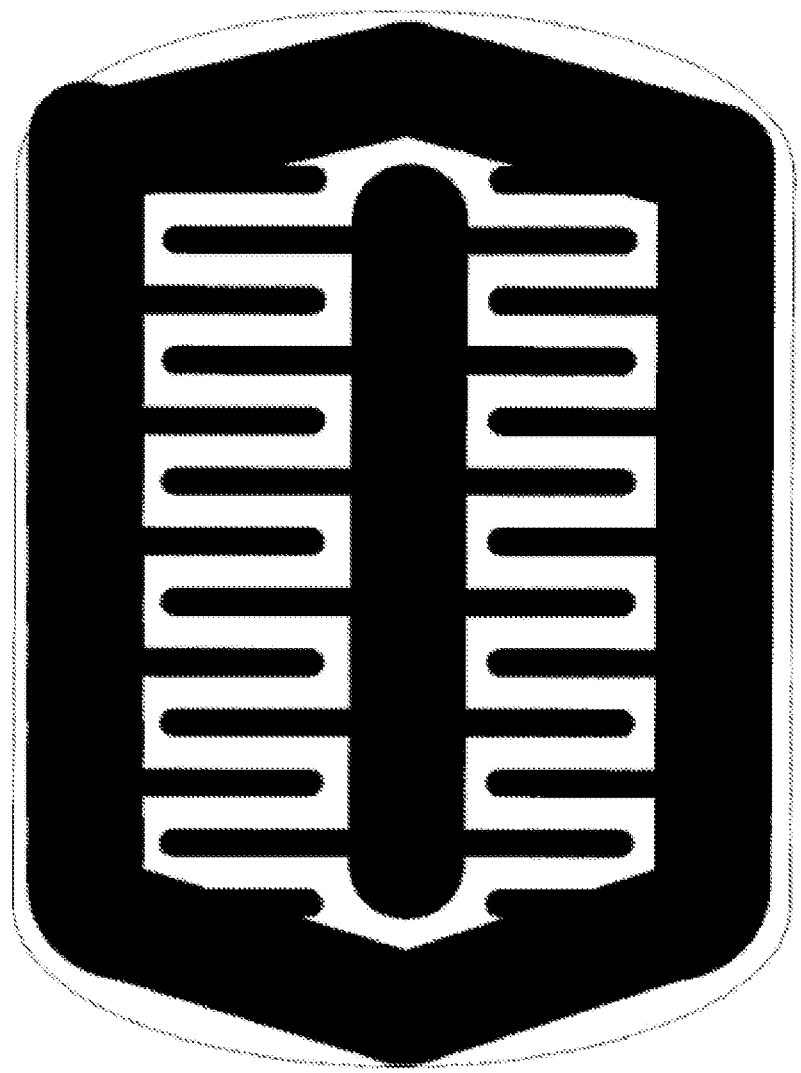
Figure 2C:
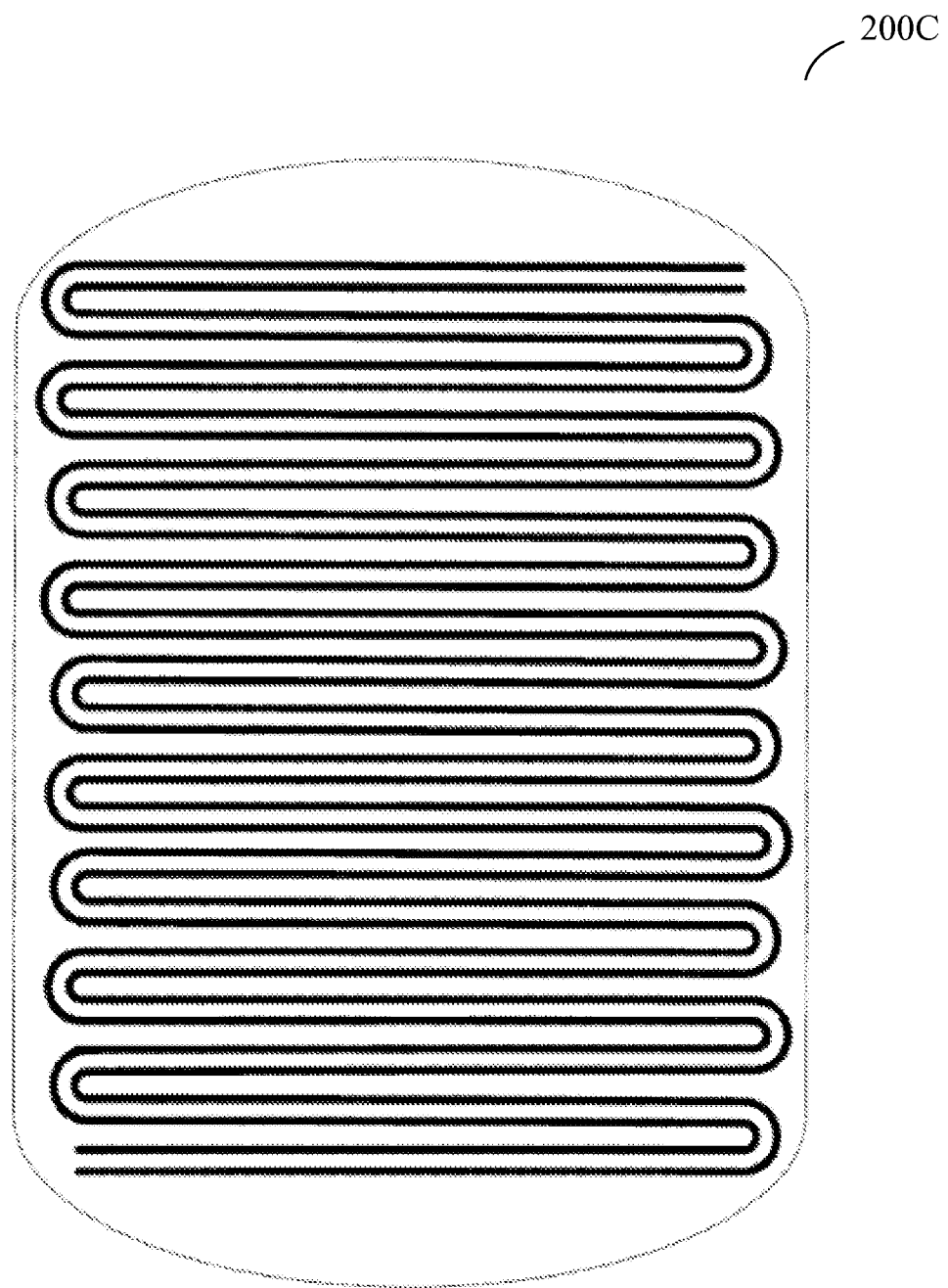
Figure 2D:
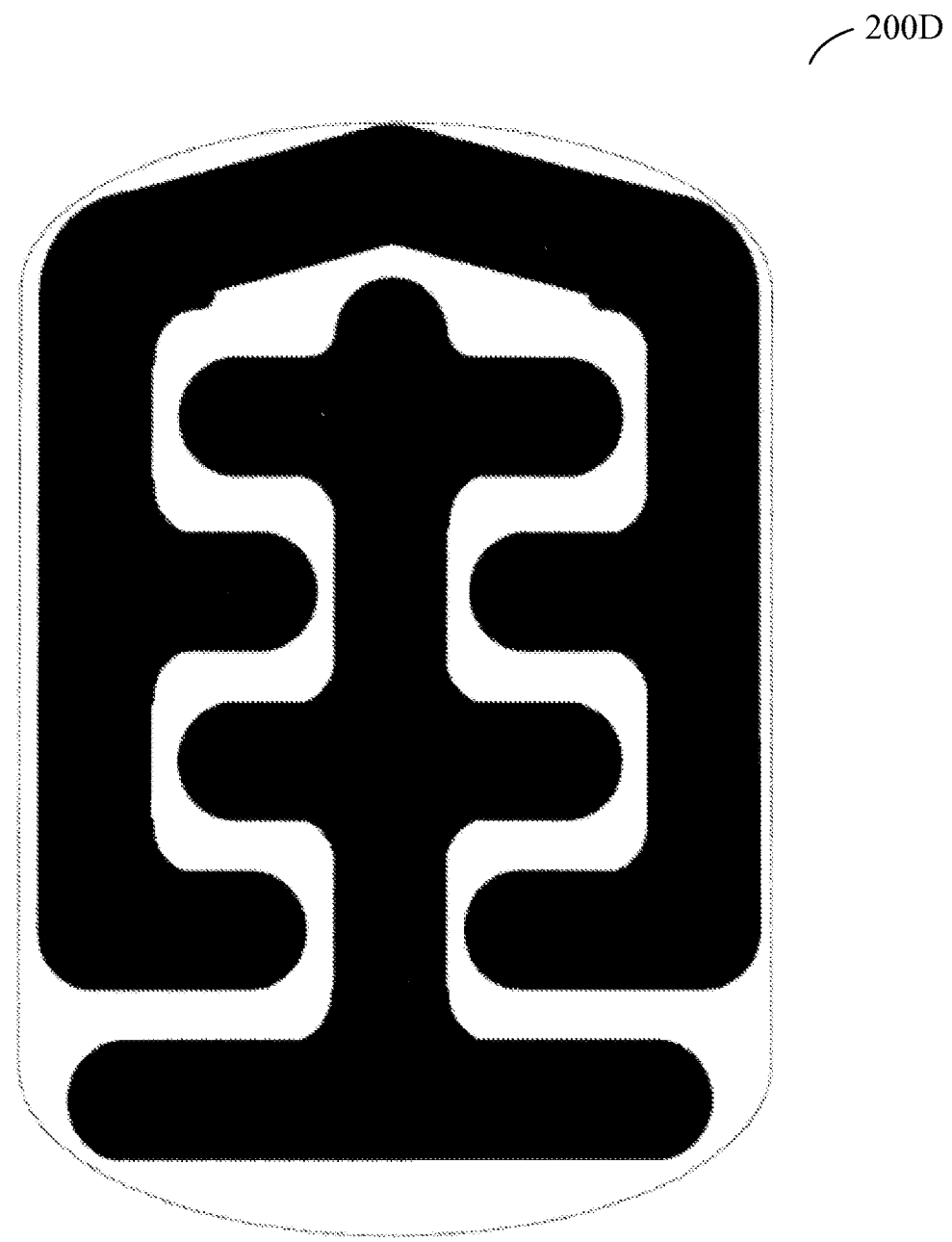
Figure 2E:
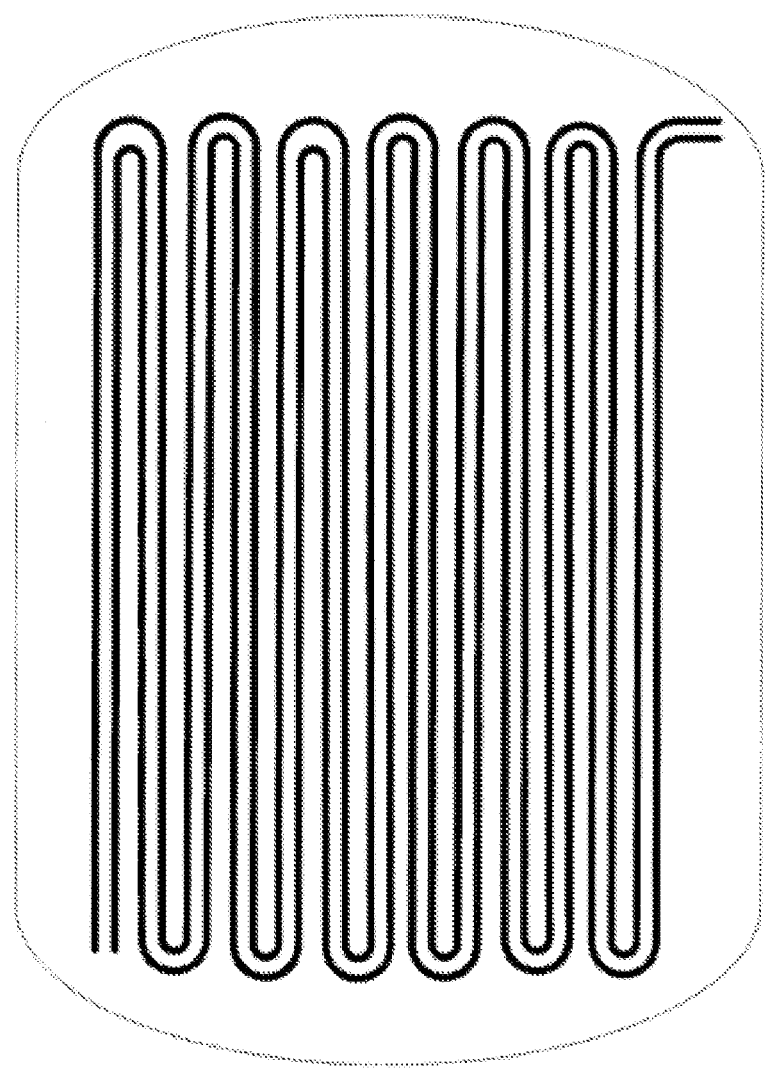
Figure 2F:
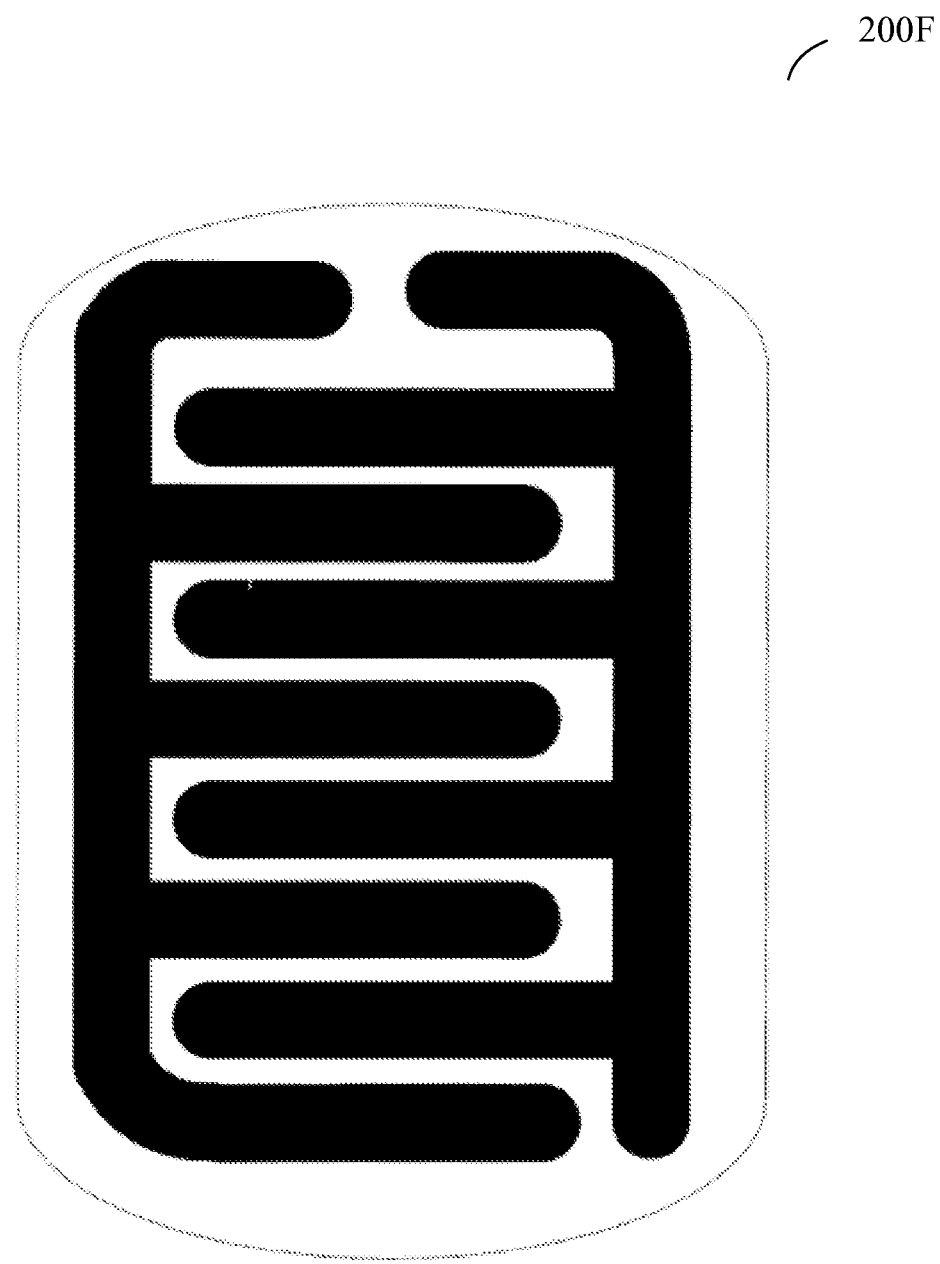
Figure 2G:
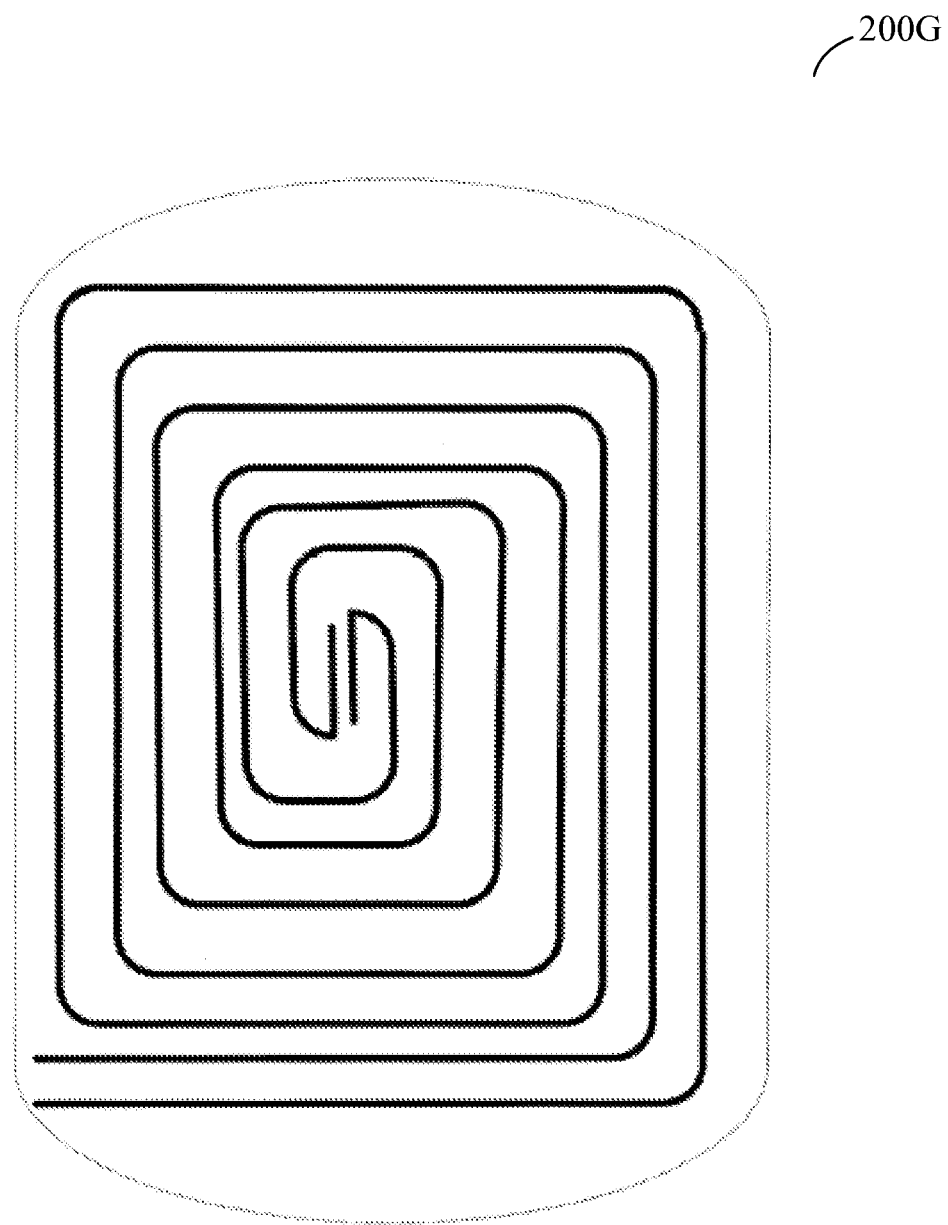
Figure 2H:
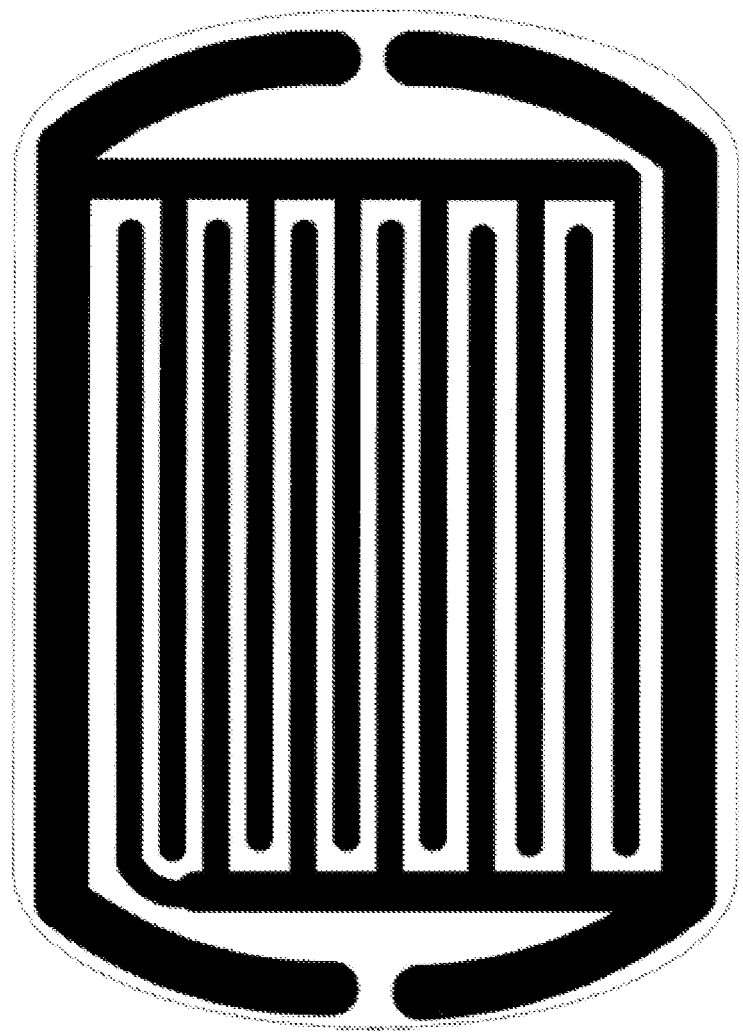
Figure 2I:
Figure 2J:
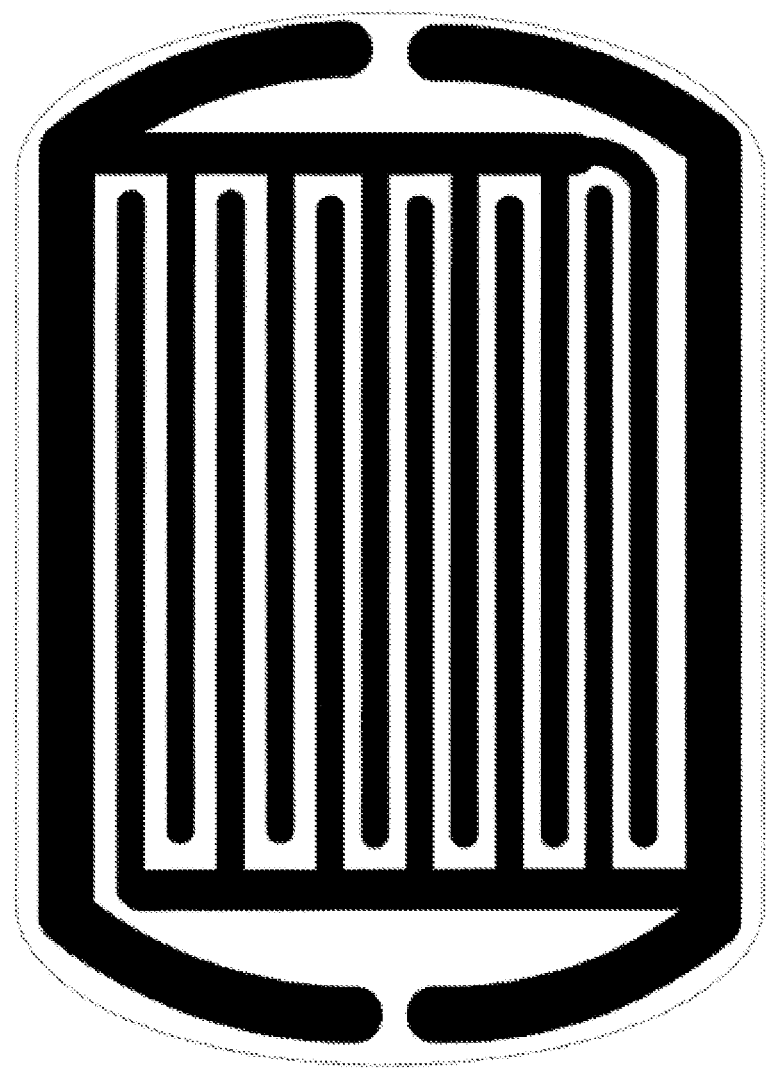
Figure 2K:
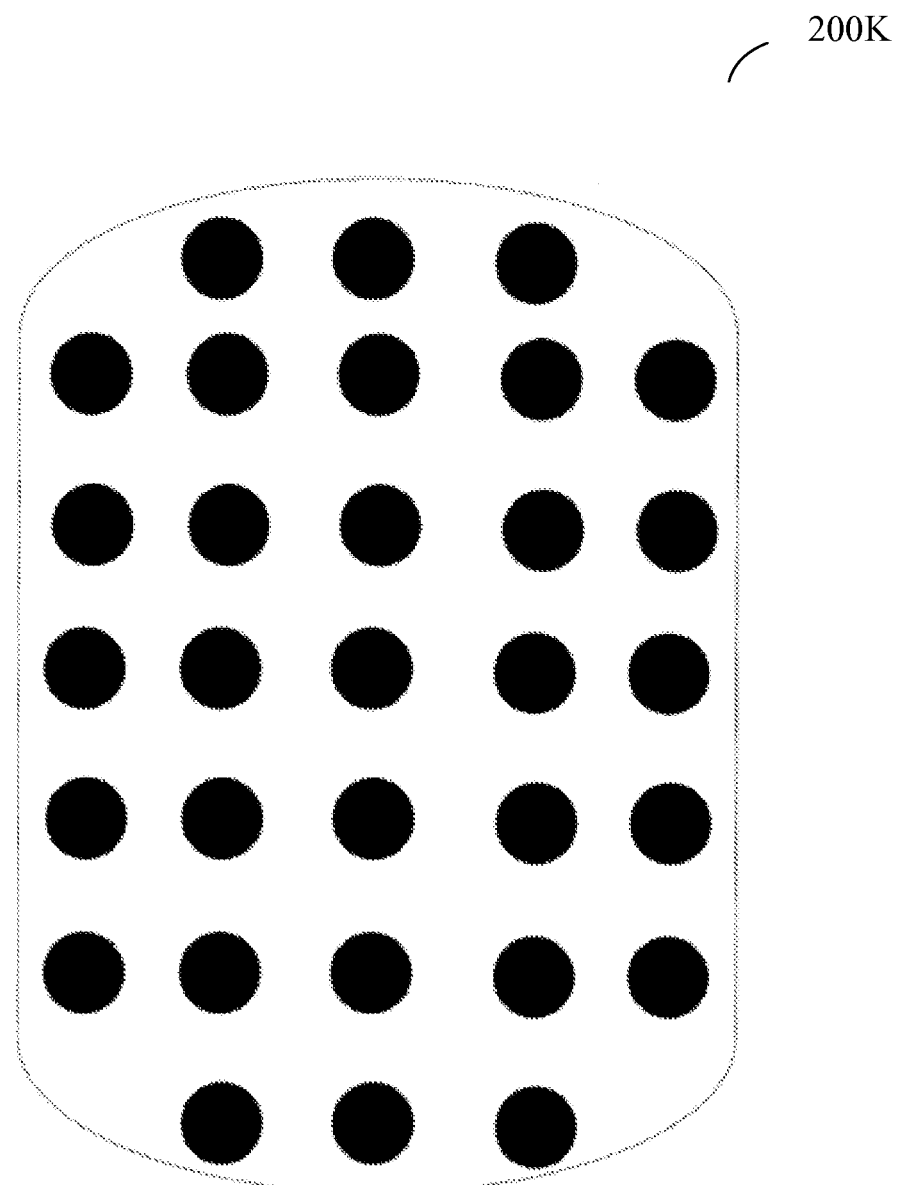

In the following description, for purposes of explanation, numerous specific details are set forth in order to provide a thorough understanding of example embodiments. It will be evident, however, to one skilled in the art, that the present solution invention may be practiced without these specific details.

The present disclosure relates to an electrolyte sensor that may be used for the detection of sweat, blood, urine, feces, saliva, and spinal fluid, which all contain electrolytes capable of enabling conduction of an electric current between electrodes. The present disclosure is also generally intended to allow the measurement of electrical resistance across electrode gaps of any possible analyte.

The advantages described herein may come by making electrolyte sensor electrodes with conductive elastomer and enjoying the properties which provide flexibility in designing electrolyte sensor shape and area (relating, for example, to penis, urine, or electrolyte source location variability), improved conductive sensitivity to electrolytes as a function of electrode area versus reaction time, sensor corrosion resistance, sensor conductive exclusivity to sweat, blood, urine, feces, or spinal fluid, sensor flexibility and comfort, and sensor durability due to heat molded construction.

The electrolyte sensor using conductive elastomer disclosed herein may be a sensor for detecting electrolytes including, but not limited to, those present in urine, sweat, saliva, feces, spinal fluid, and blood and may function as a sensor for any electrolyte. It is to be understood that the term "electrolyte" includes but is not limited to those electrolytes present in sweat, blood, urine, feces, saliva, or spinal fluid. An example of the utility for the electrolyte sensor using conductive elastomer may be in the area of enuresis treatment, when the electrolyte sensor may be attached to an alarm circuit that may be activated by the presence of urine on the electrolyte sensor. The sensor may include positive and negative conductive elastomer trace electrodes, a flexible nonconductive silicone base portion or portions, and a channel or gap or pluralities thereof separating the electrodes. The "positive" and "negative" trace electrodes are defined as those electrodes which may be respectively connected to positive and negative wire lead terminals, which may be in turn ultimately connected to positive and negative battery terminals. The conductive elastomer trace electrodes may be heat molded over a highly flexible nonconductive silicone base portion, wherein a channel or gap separates the positive trace electrode from the negative trace electrode throughout the pattern.

In some example embodiments, the flexible nonconductive silicone base portion may enable separation of the positive and negative trace electrodes and may be of a sufficient rigidity to provide a distance between the positive and negative trace electrodes.

The trace electrodes may sit on top of the flexible nonconductive silicone base portion or may be recessed into the flexible nonconductive silicone base portion. The channel or gap may comprise a spatial void using available air as a gaseous insulator or recessed electrodes may be separated by a channel or gap comprised of physical insulating material such as the silicone in the flexible nonconductive silicone base portion. Thus, the flexible nonconductive silicone base portion may enable separation of the one or more positive and negative trace electrodes. The channel or gap is not limited to an even size. Channels or gaps may be of even or uneven size or sizes throughout the trace pattern. Electrolytes, such as those present in urine, make a conductive bridge across the channel or gap between adjacent positive and negative trace electrodes causing a circuit to be closed, and the electrolytes present in urine may conduct an electric charge between the positive and negative trace electrodes. The circuit may be closed in connection with either an alarm unit or a transmitter capable of sending a signal to a remote alarm or other electronics unit. In some example embodiments, the electrolyte sensor using conductive elastomer comprises an electrolyte sensor.

In some example embodiments, the electrolyte sensor using conductive elastomer improves the speed with which an electrolyte sensor for detecting an electrolyte signals the presence of the electrolyte by making electrolyte sensor electrodes out of conductive elastomer. The conductive elastomer may conduct a current at any point along its entire surface, whereby an electrical circuit may be closed between a positive conductive elastomer electrode and a negative conductive elastomer. The positive and negative electrodes may be connected to a power source with metal wires, additional portions of conductive elastomer or in any manner. The electrical current may be supplied to the electrolyte sensor portion electrodes.

In some example embodiments, the metal wires may be connected to the positive and negative trace electrodes via wire crimps inserted into the flexible nonconductive silicone base portion by using heat vulcanization and molding.

In some example embodiments, the electrolyte sensor using conductive elastomer improves the specificity of the electrolyte sensor to react to a desired electrolyte by making electrolyte sensor electrodes out of conductive elastomer. The elastomer composition and the size of the channel or gap between trace electrodes may be a function of the amount of electrical resistance required to be overcome in forming a current across the gap.

In some example embodiments, the electrolyte sensor using conductive elastomer may improve the functional shape of a urine sensor by making urine sensor electrodes out of conductive elastomer and connecting them via a trace pattern to a highly flexible nonconductive silicone base portion, whereby a penis can change positioning during the night, and conductive elastomer trace electrodes can be patterned to detect urine over a useful area of virtually any shape.

In some example embodiments, the electrolyte sensor using conductive elastomer improves the state of the art of electrolyte detection by lessening the amount of electrolyte required to activate an electrolyte sensor by making electrolyte sensor electrodes out of conductive elastomer.

In some example embodiments, the electrolyte sensor using conductive elastomer improves the flexibility of electrolyte sensors by making electrolyte sensor electrodes out of conductive elastomer and with a flexible nonconductive silicone base portion or bridge portions.

In some example embodiments, the electrolyte sensor using conductive elastomer improves the comfort of electrolyte sensors worn by users by making electrolyte sensor electrodes out of conductive elastomer and a base portion out of flexible silicone by virtue of inherent properties of elastomer including relative warmth to the touch, and with the silicone base portion having soft rounded edges and corners. Also adding to the comfort is the replacement of metal in the electrolyte sensor surface with elastomer, thereby minimizing the use of hard, sharp materials in electrolyte sensor construction.

In some example embodiments, the electrolyte sensor using conductive elastomer improves the durability of electrolyte sensors through heat molding electrolyte sensor electrodes and lead wires to a flexible nonconductive silicone base portion.

In some example embodiments, the electrolyte sensor using conductive elastomer improves the corrosion resistance of electrolyte sensors by making electrolyte sensor electrodes out of conductive elastomer instead of metal wires.

The chemical process for producing conductive elastomer is well known and principally comprises mixing elastomer with conductive particles. It should be understood that numerous equivalent compounds could be used to create elastomeric compounds capable of forming a suitable positive or negative electrode. Additionally, the compounds used may be classified as polymeric as opposed to elastomeric. The preferred embodiment of the elastomer composition for the present disclosure is indicated in a table below.

The characteristics and utilities of the example embodiments described in this detailed description and in the summary above are not all inclusive. Many additional features and advantages will be apparent to one of ordinary skill in the art given the following drawings, specifications and claims.

FIG. 1 is a perspective view illustrating the incoming wire lead terminals 50, 70 attached to a base portion 110 and the trace electrodes 150, 170. The trace electrodes 150, 170 may be separated physically and electrically by a channel or gap 120, which may be then filled with electrolyte, whereby a circuit may be closed.

Means for separating positive and negative trace electrodes 150, 170 in order to maintain a desired distance or distances between the trace electrodes include, but are not limited to, the method of heat molding the trace electrodes 150,170 to the base portion 110 at the desired distance or distances from each other, and alternatively the use of nonconductive "bridges" between the trace electrodes, wherein a base portion may or may not be used. An example embodiment is the use of a flexible nonconductive silicone base portion wherein the incoming wire lead terminals 50, 70 may be connected to the trace electrodes 150,170 by heat molding to the trace electrodes 150,170 and the base portion 110 to prevent or make difficult the dislodgement of the wire lead terminals 50, 70 in use. Bare wire lead terminals 50, 70 may be positioned proximally to a portion of a respective electrode. Silicone from the silicone base portion 110 may be melted around the bare wire lead terminals 50, 70 and the connection may be vulcanized. Heat molding wire lead terminals to electrodes has an additional advantage of freeing the manufacture of the electrolyte sensor from physical and financial constraints associated with shaping metal wires into a trace pattern in favor of an elastomer trace mold.

Heat molding may also be the means for connecting the wire lead terminals 50, 70 to the silicone base portion 110. The present disclosure also anticipates use of rivets, wire crimps, screws, frictional, and/or compression connecting means.

It is anticipated that the wire lead terminals 50, 70 may be connected directly to an alarm or other electronic unit or that the wire lead terminals 50, 70 may be connected to a transmitter unit, which may transmit to a remote alarm or other electronics unit. It is separately anticipated that the electrolyte sensor 100 may have more than one sensing surface, and the silicone base portion 110 may contain more than one surface upon which to place elastomer trace electrodes with same or different trace patterns on the surfaces.

The positive and negative conductive elastomer trace electrodes 150,170 may be arranged with the channel or gap 120 separating the positive and negative trace electrodes 150,170. The channel or gap distance may be defined as the distance between the positive electrode 150 or a portion thereof and the nearest negative electrode 170 or a portion thereof. The size of the channel or gap distance between the trace electrodes 150,170 may be defined as a functional size that may be determined by the conductive ability of electrolytes to quickly form a circuit bridge between the positive and negative conductive elastomer trace electrodes 150,170, whereas without the electrolytes the channel or gap distance size will cause the circuit to remain open. It is anticipated that the electrolytes can bridge positive and negative electrodes that are not only one channel or gap distance from each other but may alternatively bridge positive and negative trace electrodes separated by numerous channels or gaps, or may employ channel or gap distances of uneven size or sizes. It is therefore established that the anticipated embodiments of the channel or gap distance between the trace electrodes 150,170, and the related embodiments of trace widths or areas, are to be understood to comprise a functional value limited only by the conductivity of a given electrolyte across a certain distance and between the trace electrodes 150,170 carrying current of a certain resistance level. The non-limiting example embodiment for the distance between positive and negative trace electrodes 150, 170 comprising the channel or gap distance may be 1-20 mm, and an example embodiment for the size of trace widths or diameters may be 1-20 mm.

It is also to be understood that the present disclosure anticipates an embodiment wherein nonconductive silicone or an equivalent material may be employed to form small bridges placed at functional intervals that function to separate the conductive elastomer trace electrodes 150,170 from each other, thereby establishing and maintaining the channel or gap 120 or a plurality of channels or gaps between electrodes. However, it is the preferred embodiment of the present disclosure to utilize the flexible nonconductive silicone base portion 110 as the separation means to create a channel or gap between the trace electrodes 150,170. The conductive elastomer trace electrodes 150,170 may be attached to the flexible nonconductive silicone base portion 110 in such a manner that a channel or gap may be established between them. The attachment means for attaching the trace electrodes 150,170 to the flexible nonconductive silicone base portion 110 may be heat molding. The preferred compositions for the conductive elastomer trace electrodes 150,170 and the silicone base portion 110 are shown in the tables below:

| Conductive Elastomer | | |
|---|---|---|
| Silicone: | methyl vinyl silicone rubber (dimethyl polysiloxane) | 57% |
| Conductive Carbon Black: | acetylene carbon (acetylene black) | 42% |
| Hardener: | 2.5-2.5-2-methyl t-butyl peroxy-2 ethane (dimethyl-2.5- di (tertiary-butyl peroxy)hexane) | 1% |

| Insulating Rubber Silicone Base Portion (Electrolyte Sensor Base Portion) | | |
|---|---|---|
| Silicone: | methyl vinyl silicone rubber (dimethyl polysiloxane) | 99% |
| Hardener: | 2.5-2.5-2-methyl t-butyl peroxy-2 ethane (dimethyl-2.5- di (tertiary-butyl peroxy)hexane) | 1% |

It is further to be understood that the present disclosure anticipates unequal size gaps or channel distances, as well as varying trace sizes in the same electrolyte sensor. However, the preferred embodiment is to have trace electrode patterns with channel or gap distances and/or trace widths or diameters that operate within a size range as needed for detection of a given electrolyte. See FIGS. 2A-2K.

FIGS. 2A-2K show various electrode trace patterns as examples of the patterns provided by the present disclosure.

Given the above functional definition for electrode trace embodiments, it is possible for numerous trace patterns with correlating channels or gaps between positive and negative conductive elastomer trace electrodes to function equivalently. Some of these examples 200A, 200B, 200C, 200D, 200E, 200F, 200G, 200H, 200I, 200J, and 200K are represented in FIGS. 2A-2K. It is to be understood, therefore, that those trace patterns using the above functional definition are equivalents to one another, and that the preferred embodiment is to be understood more precisely as a range of values for channel or gap distance and related trace width or area (diameter).

Figure 3:
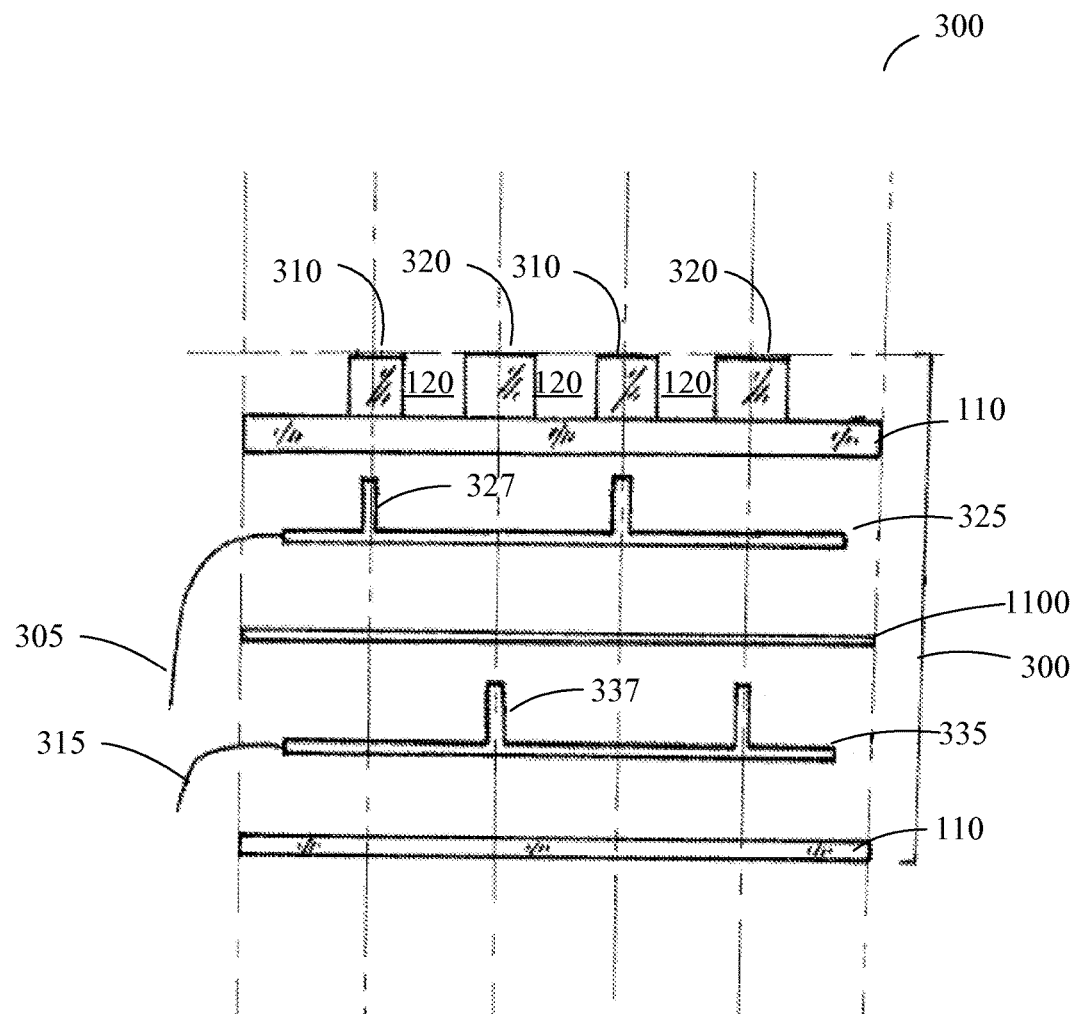
FIG. 3 is an exploded side view of an electrolyte sensor with an island type electrode pattern, in accordance with an example embodiment.

FIG. 3 is an exploded side view of an electrolyte sensor 300 with an island type electrode pattern. Along with linear style trace electrodes, herein referred to as "trace electrodes," is an additional embodiment for electrode pattern design comprising a plurality of spaced apart "electrode islands," herein referred to as "islands." See FIG. 2L and FIG. 3. Electrolyte sensor composition, wherein an island pattern may be used, comprises connecting wire lead terminals 305, 315 to separate positive and negative overlaid planar conductive grids 325, 335 that may be separated from each other by an insulating layer 1100 within the base portion 110. The planar grids 325, 335 have corresponding small positive and negative posts 327, 337 that protrude perpendicularly from the planar grids 325, 335 and through insulating material to an outer surface of the base portion 110. The positive and negative protruding posts 327, 337 may be positionally offset from one another and an elastomer may be heat molded to each. The result may be a plurality of elastomeric island electrodes 310, 320 that may be alternating cylindrical or non-cylindrical positive and negative electrodes separated physically and electrically by gaps 120, which may be then filled with electrolyte, whereby a circuit may be closed.

Figure 4:
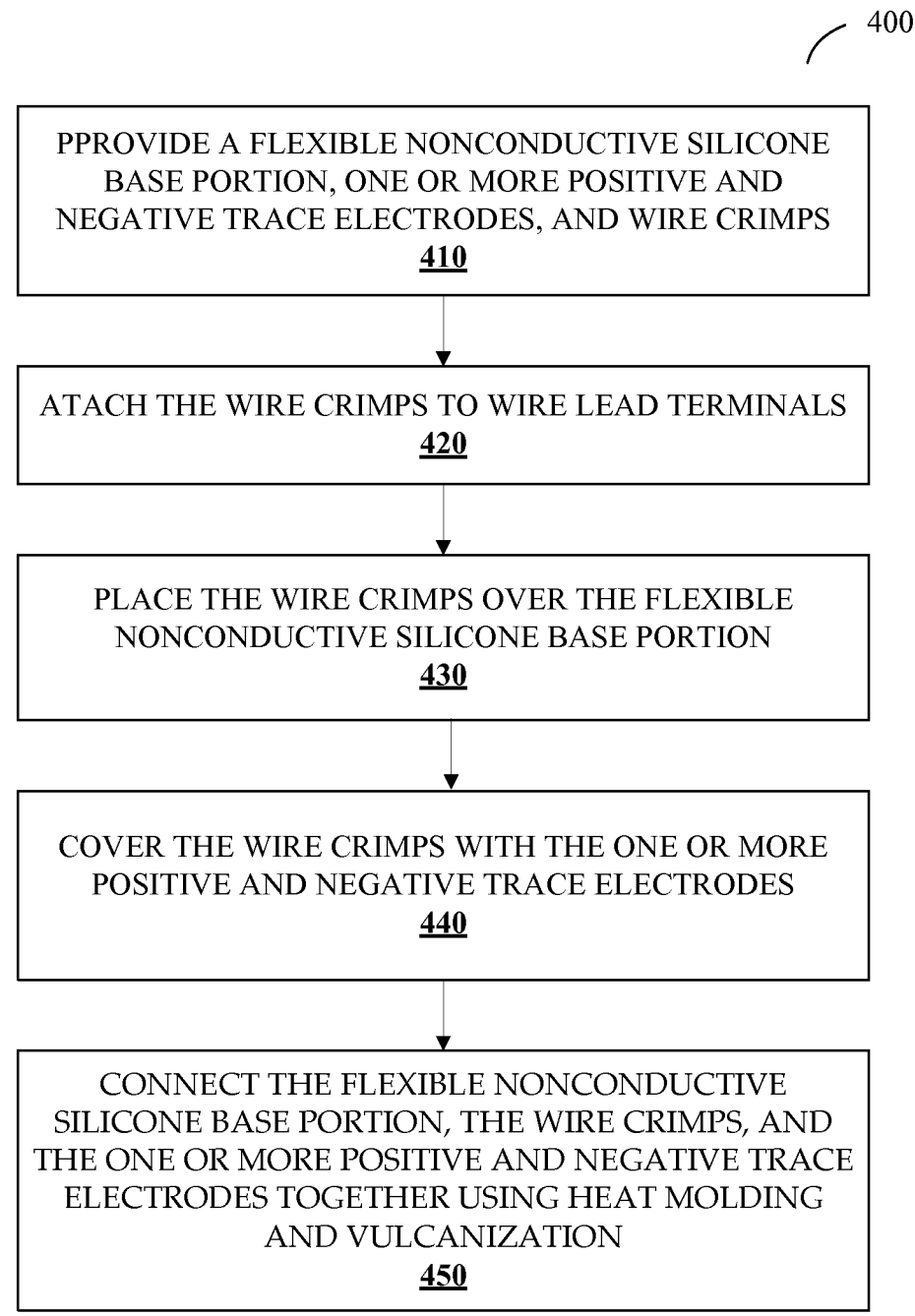
FIG. 4 is a flow chart illustrating a method for producing an electrolyte sensor, in accordance with an example embodiment.

FIG. 4 is a flowchart illustrating a method 400 for producing an electrolyte sensor, in accordance with an example embodiment.

The method 400 may commence with providing a flexible nonconductive silicone base portion, one or more positive and negative trace electrodes, and wire crimps, at operation 410.

The method 400 may further proceed with attaching the wire crimps to wire lead terminals, at operation 420. The wire crimps may be designed to receive wire lead terminals, which may, in turn, be connected to respective positive and negative battery terminals.

At operation 430, the wire crimps may be placed over the flexible nonconductive silicone base portion. The wire crimps may then be covered with the one or more positive and negative trace electrodes, at operation 440.

At operation 450, the flexible nonconductive silicone base portion, the wire crimps and the one or more positive and negative trace electrodes may be connected together using heat molding and vulcanization. The flexible nonconductive silicone base portion may enable separation of the one or more positive and negative trace electrodes. The one or more positive and negative trace electrodes may include a conductive polymer and may be arranged in a pattern of proximity with respect to each other throughout a surface of the electrolyte sensor.

The method 400 may optionally include fusing a single piece of a cable to the electrolyte sensor through a strain relief.

Figure 5:
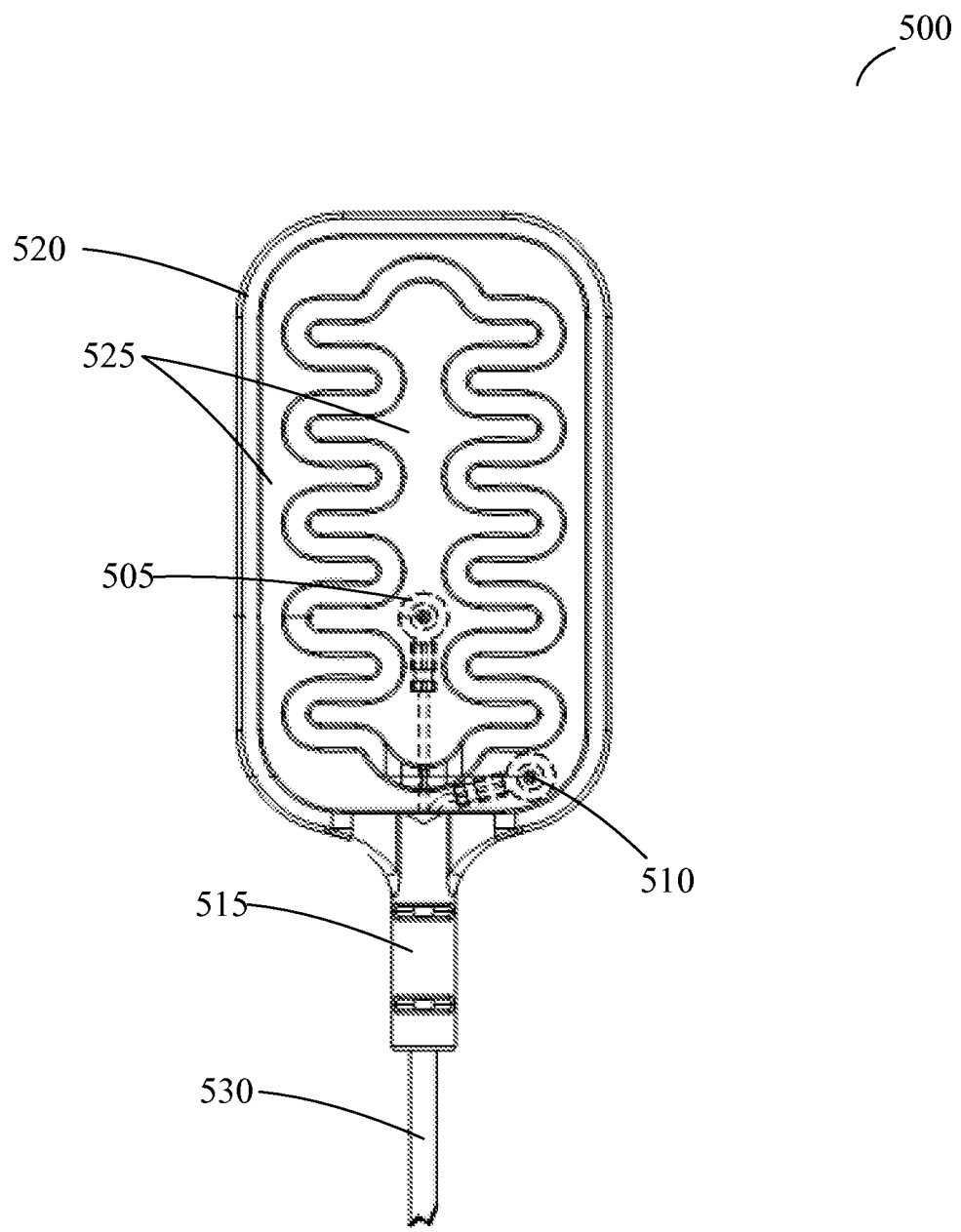
FIG. 5 is a schematic representation of an electrolyte sensor illustrating how wire crimps may connect to conductive elastomer electrodes, in accordance with an example embodiment.

FIG. 5 is a schematic representation of an electrolyte sensor 500 illustrating how wire crimps may connect to conductive elastomer electrodes. The electrolyte sensor 500 may comprise a flexible nonconductive silicone base portion 520 and one or more positive and negative trace conductive elastomer electrodes 525. The flexible nonconductive silicone base portion 520 may enable separation of the one or more positive and negative trace electrodes 525. The wire crimps may be of any size and shape suitable for receiving wire lead terminals. For example, the wire crimps 505, 510 may include two metal rings that may be placed on the flexible nonconductive silicone base portion during a heat vulcanization manufacturing process. These metal rings may be tied around wire lead terminals in the conductive elastomer electrodes 525 to increase durability and pull strength. The wire lead terminals may be inserted during heat vulcanization.

According to one example embodiment, the electrolyte sensor 500 may be a single silicone base portion 520 with conductive elastomer electrodes 525 and a single piece of cable fused to the electrodes using a strain relief 515. The strain relief 515 may be a part of the extended portion of the electrolyte sensor 500 and may be wrapped around a cable 530 for increased strength.

According to one example embodiment, due to the configuration of the electrolyte sensor components and the manufacturing process described above, the electrolyte sensor 500 may be thinner than 5 mm.

Figure 6:
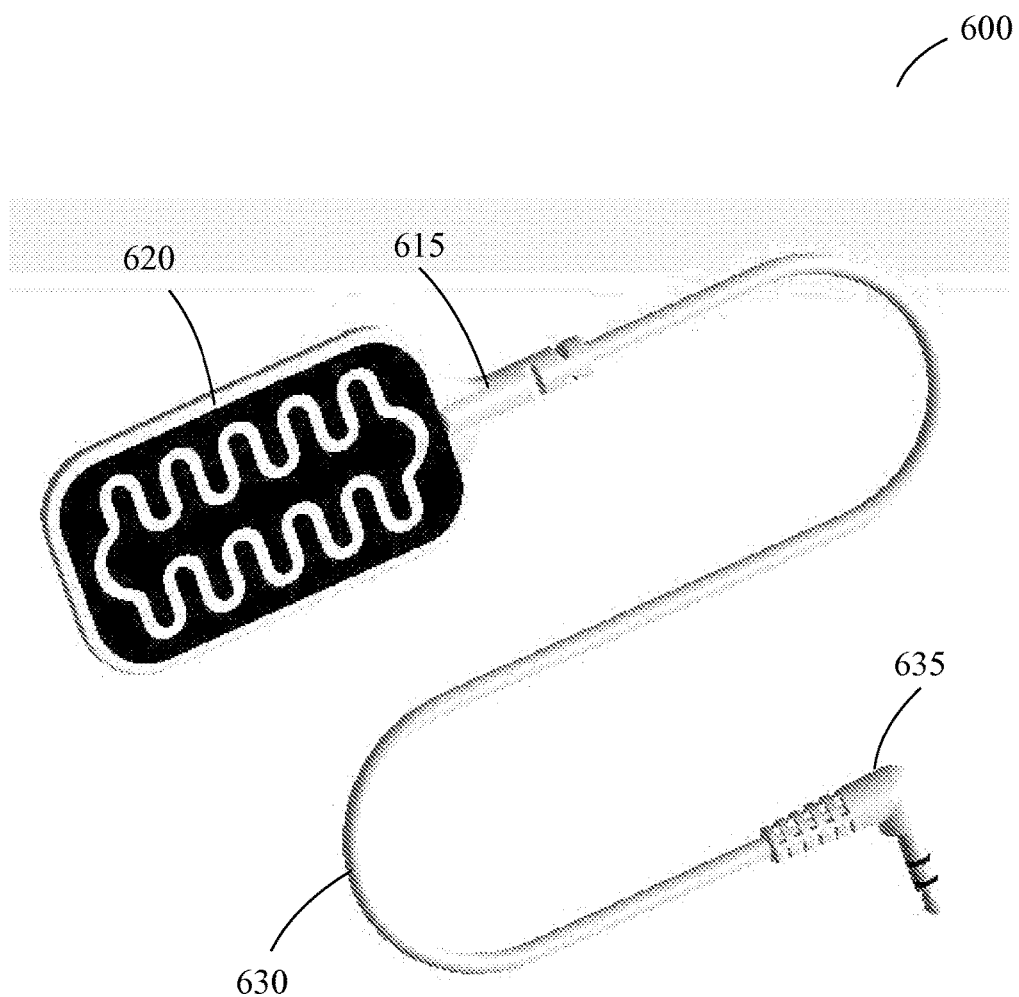
FIG. 6 is an overall view of an electrolyte sensor, in accordance with an example embodiment.

FIG. 6 is an overall view of an electrolyte sensor 600, in accordance with an example embodiment.

The electrolyte sensor 600 may comprise a main portion 620 formed of a flexible nonconductive silicone base portion and trace electrodes. Attached to the main portion 620 may be a two-wired cable 630, with each wire connected to a negative trace electrode and a positive trace electrode correspondingly. One end of the cable 630 may be fused to the main portion 620 of the electrolyte sensor 600 via a strain relief 615 such that no liquid can penetrate inside. The other end of the cable 630 may have a plug 635.

Figure 7:
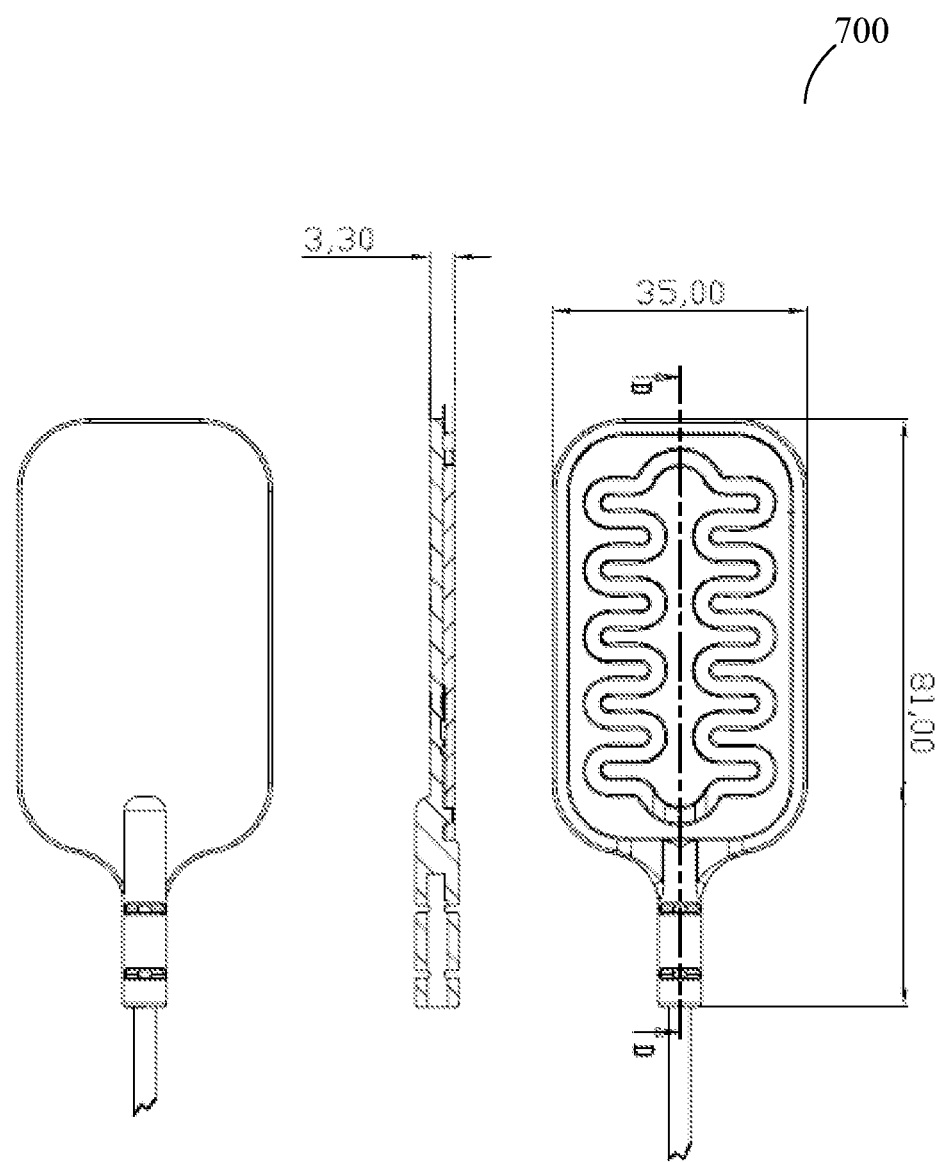
FIG. 7 is a schematic representation of a particular embodiment of an electrolyte sensor.

FIG. 7 is a schematic representation 700 of a particular embodiment of an electrolyte sensor.

In particular, FIG. 7 shows the front view, back view, and side view of the electrolyte sensor. The electrolyte sensor depicted on FIG. 7 may have the following dimensions: length (from the top to the end of a strain relief)—81 mm, width—35 mm, and thickness—3.30 mm.

Figure 8:
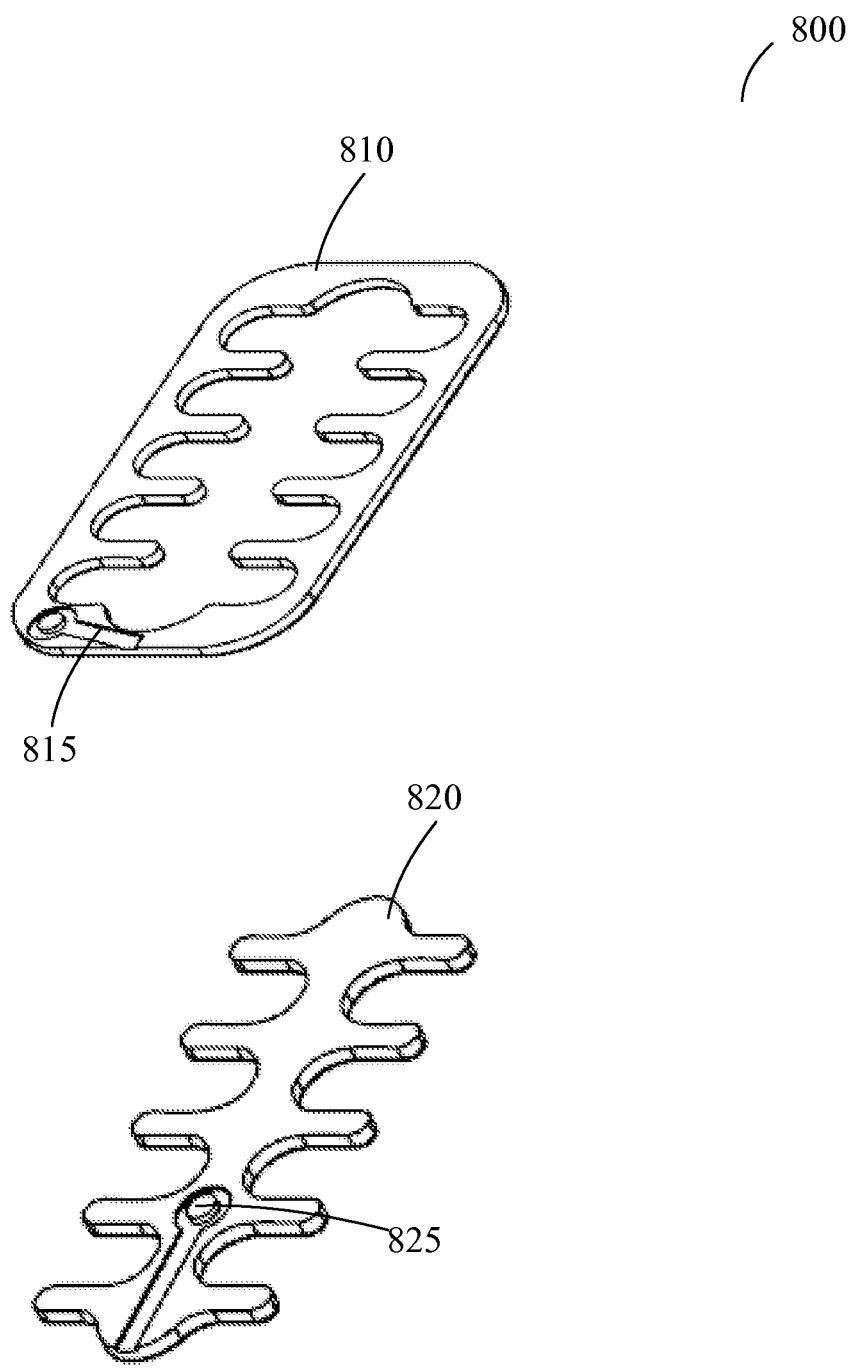
FIG. 8 is an overall view of positive and negative trace electrodes of an electrolyte sensor, in accordance with an example embodiment.

FIG. 8 is an overall view 800 of positive and negative trace conductive elastomer electrodes 810, 820 of an electrolyte sensor, in accordance with an example embodiment. Both trace electrodes 810, 820 may comprise, in their lower parts, wire crimps 815, 825 suitable for receiving wire lead terminals, which may be in turn ultimately connected to positive and negative battery terminals. The inner shape of the elastomer electrode 810 may be designed to fit the outer counter of the elastomer electrode 820.

Figure 9:
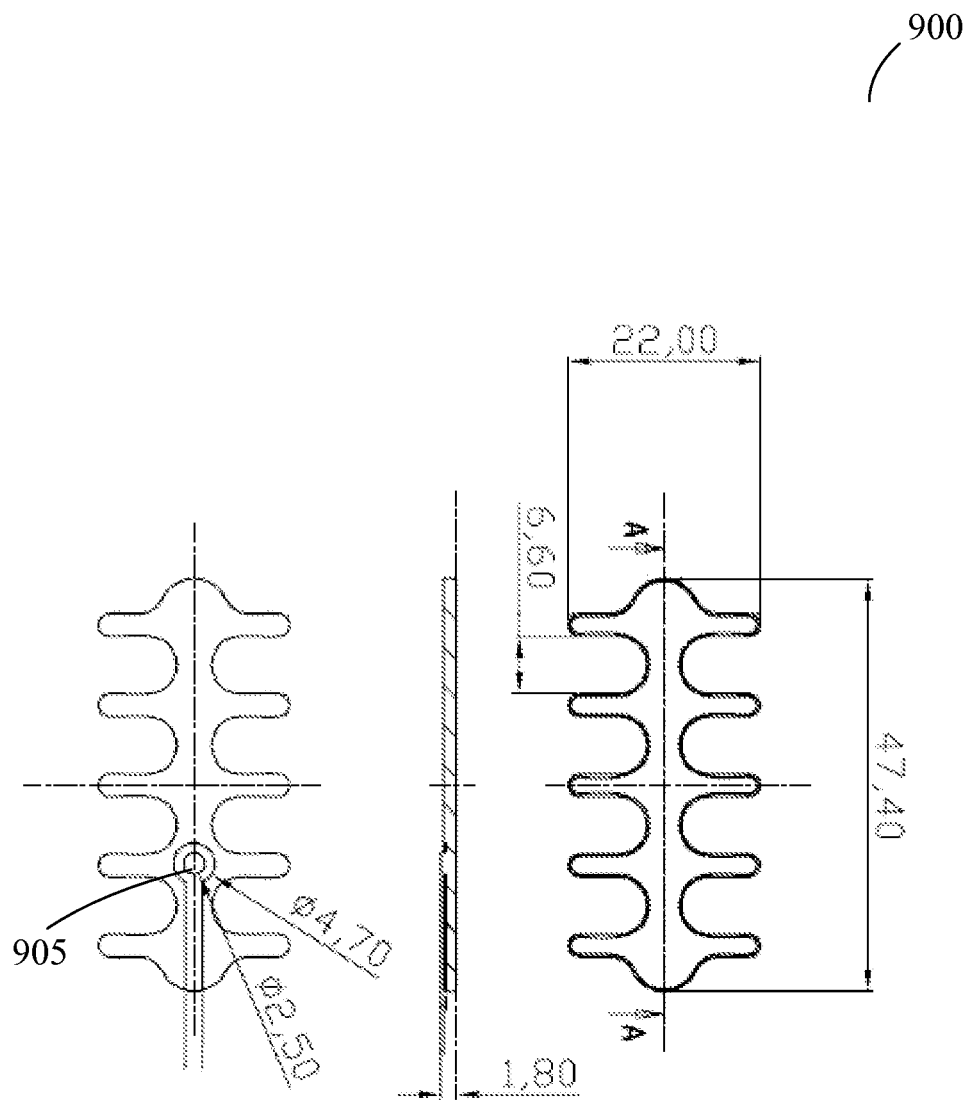
FIG. 9 is a schematic representation of one of the trace electrodes depicted in FIG. 8, in accordance with an example embodiment.

FIG. 9 is a schematic representation of the trace electrode 900 corresponding to the trace electrode 820 depicted in FIG. 8, in accordance with an example embodiment. As shown in FIG. 9, the trace electrode may have the following dimensions: length—47.4 mm, width—22 mm, thickness—1.8 mm. The trace electrode 900 is shown to have five pairs of symmetric legs. The distance between two adjacent legs may be 6.6 mm. The trace electrode comprises a wire crimp 905 arranged in the lower portion of the trace electrode along its longitudinal axis. The wire crimp 905 may comprise an apertured circular head with the inner diameter 2.5 mm the outer diameter 4.7 mm.

Figure 10:
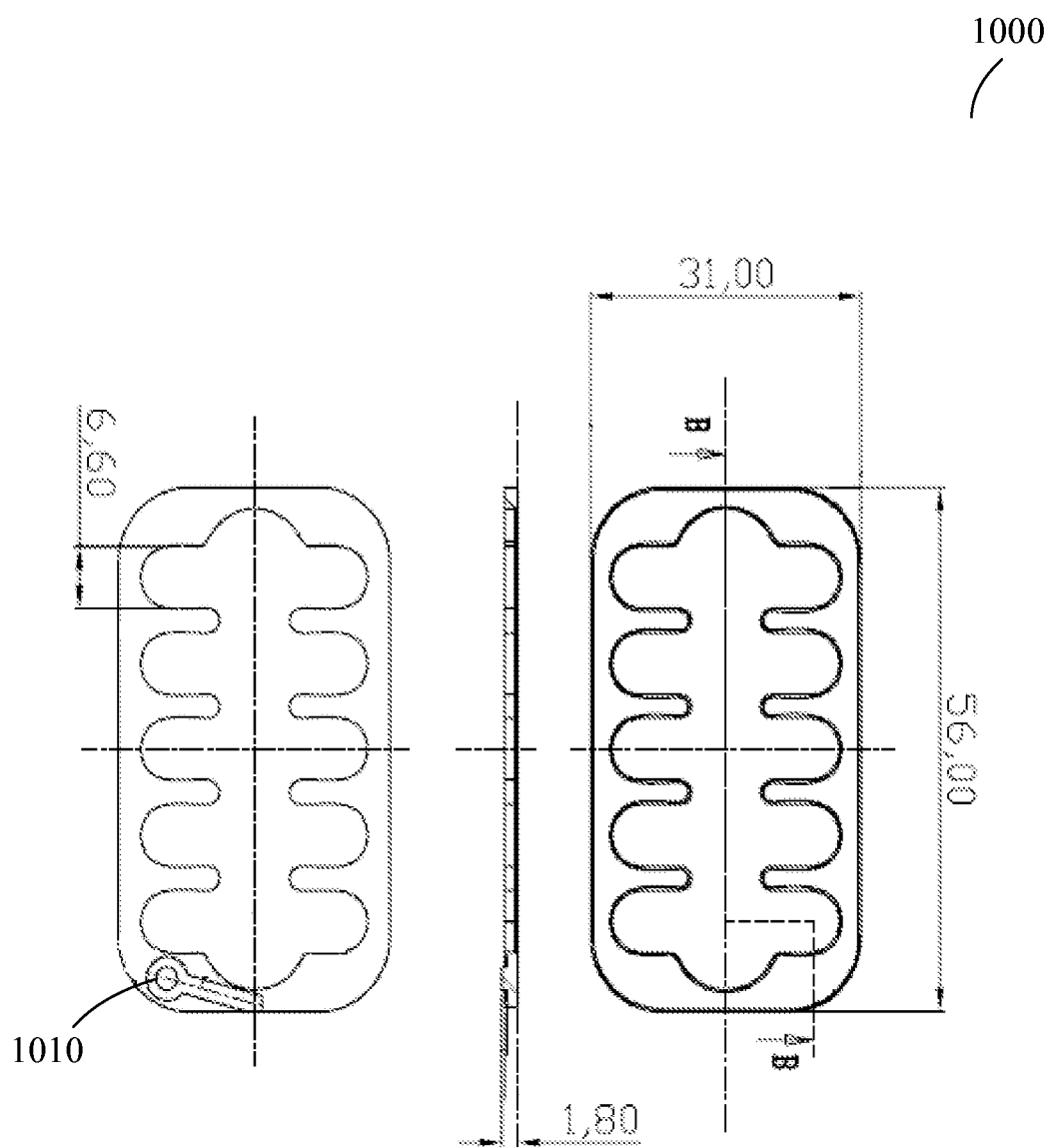
FIG. 10 is a schematic representation of a flexible nonconductive silicone base portion forming a part of an electrolyte sensor, in accordance with an example embodiment.

FIG. 10 is a schematic representation of the trace electrode 1000 corresponding to the trace electrode 810 depicted in FIG. 8, in accordance with an example embodiment. As shown in FIG. 10, the trace electrode may have the following dimensions: length—56 mm, width—31 mm, and thickness—1.8 mm. The trace electrode is shown to have five pairs of symmetric cavities. The width of each cavity may be 6.6 mm. The trace electrode comprises a wire crimp 1010 arranged in the lower portion of the trace electrode at an angle to its longitudinal axis. The wire crimp 1010 may be similar to the wire crimp 905 shown in FIG. 9.

Figure 11:
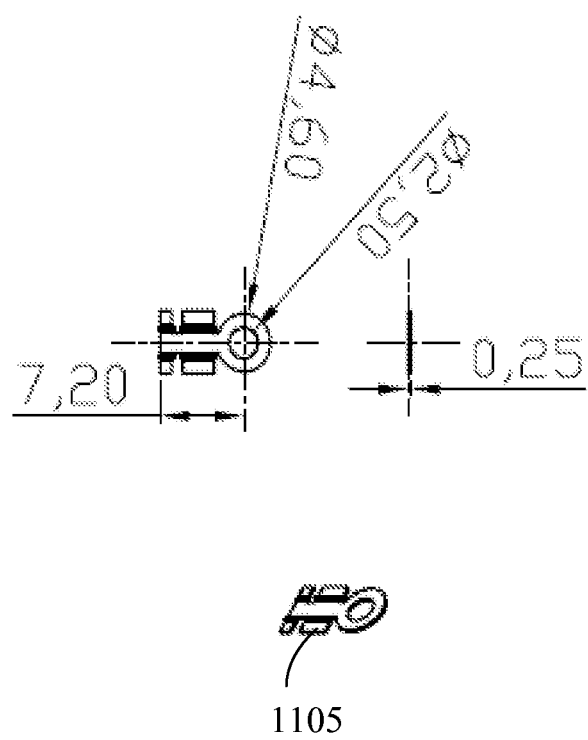
FIG. 11 is a schematic representation of a wire crimp of an electrolyte sensor, in accordance with an example embodiment.

FIG. 11 is a schematic representation of a wire crimp 1105 of an electrolyte sensor, in accordance with an example embodiment.

The wire crimp 1105 may be designed to receive a respective wire lead terminals. As shown on FIG. 11, the wire crimp 1105 may have an apertured circular head with the inner diameter 2.5 mm and the outer diameter 4.6 mm. The dimensions of the wire crimp 1105 may be the following: the length from one end to the center of the circular head—7.2 mm, the thickness—0.25 mm.

Thus, embodiments of the electrolyte sensor using conductive elastomer have been described. Although the embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

What is claimed is:

1. An electrolyte sensor for detecting an analyte, the electrolyte sensor comprising:
   a flexible nonconductive silicone base portion; wire crimps attached to wire lead terminals, wherein the wire crimps are arranged on the flexible nonconductive silicone base portion;
   one or more positive and negative electrodes covering the wire crimps, wherein the flexible nonconductive silicone base portion, the wire crimps, and the one or more positive and negative electrodes are connected together by using heat molding and vulcanization,
   the flexible nonconductive silicone base portion enabling separation of the one or more positive and negative electrodes,
   the one or more positive and negative electrodes including a conductive polymer and arranged in proximity to each other throughout at least a portion of a surface of the electrolyte sensor;
   wherein the one or more positive and negative electrodes are disposed in a void defined by the flexible silicon base portion, whereby the proximity of the positive and negative electrodes provides a restrictive channel within which a liquid can flow along the surface.

2. The electrolyte sensor of claim 1, wherein the wire lead terminals are connected to respective positive and negative battery terminals.

3. The electrolyte sensor of claim 1, wherein the conductive polymer is an elastomer.

4. The electrolyte sensor of claim 1, wherein the proximity between the one or more positive and negative electrodes is sufficient to prevent conducting of an electric current between the one or more positive and negative electrodes.

5. The electrolyte sensor of claim 1, wherein the proximity is formed by one or more channels or gaps of an uneven dimension.

6. The electrolyte sensor of claim 5, wherein the one or more positive and negative electrodes form islands throughout the surface, the one or more channels or gaps separating the islands.

7. The electrolyte sensor of claim 5, wherein the one or more channels or gaps are of sufficient sizes to allow analyte present in a solid, liquid or gas to conduct electricity between the one or more positive and negative electrodes.

8. The electrolyte sensor of claim 1, wherein the one or more positive and negative electrodes are separated by one or more bridges.

9. The electrolyte sensor of claim 1, wherein the flexible nonconductive silicone base portion is of a sufficient rigidity to provide a distance between the one or more positive and negative electrodes.

10. A method for producing an electrolyte sensor for detecting an analyte, the method comprising:
    providing a flexible nonconductive silicone base portion, one or more positive and negative electrodes, and wire crimps;
    attaching the wire crimps to wire lead terminals;
    placing the wire crimps over the flexible nonconductive silicone base portion;
    covering the wire crimps with the one or more positive and negative electrodes;
    connecting the flexible nonconductive silicone base portion, the wire crimps and the one or more positive and negative trace electrodes together using heat molding and vulcanization,
    the flexible nonconductive silicone base portion enabling separation of the one or more positive and negative electrodes,
    the one or more positive and negative electrodes including a conductive polymer and arranged in proximity to each other throughout at least a portion of a surface of the electrolyte sensor;
    wherein the one or more positive and negative electrodes are disposed in a void defined by the flexible silicon base portion, whereby the proximity of the positive and negative electrodes provides a restrictive channel within which a liquid can flow along the surface.

11. The method of claim 10, further comprising fusing a single piece of a cable to the electrolyte sensor through a strain relief.

12. The method of claim 10, further comprising connecting the wire lead terminals to respective positive and negative battery terminals.

13. The method of claim 10, wherein the conductive polymer is an elastomer.

14. The method of claim 10, wherein the proximity between the one or more positive and negative electrodes is sufficient to prevent conducting of an electric current between the one or more positive and negative electrodes.

15. The method of claim 10, wherein the proximity is formed by one or more channels or gaps of an uneven dimension.

16. The method of claim 15, wherein the one or more positive and negative electrodes form islands throughout the surface, the one or more channels or gaps separating the islands.

17. The method of claim 15, wherein the one or more channels or gaps are of sufficient sizes to allow analyte present in a solid, liquid or gas to conduct electricity between the one or more positive and negative electrodes.

18. The method of claim 10, wherein the one or more positive and negative electrodes are separated by one or more bridges.

19. The method of claim 10, wherein the flexible nonconductive silicone base portion is of a sufficient rigidity to provide a distance between the one or more positive and negative electrodes.

20. An electrolyte sensor for detecting an analyte, the electrolyte sensor comprising:
    a flexible nonconductive silicone base portion; wire crimps attached to wire lead terminals, wherein the wire crimps are arranged on the flexible nonconductive silicone base portion;
    one or more positive and negative electrodes covering the wire crimps, wherein the flexible nonconductive silicone base portion, the wire crimps, and the one or more positive and negative trace electrodes are connected together by using heat molding and vulcanization,
    the flexible nonconductive silicone base portion enabling separation of the one or more positive and negative electrodes,
    the one or more positive and negative electrodes including an elastomer and arranged in proximity to each other throughout at least a portion of a surface of the electrolyte sensor, wherein the proximity is formed by one or more channels or gaps of an uneven dimension;

wherein the one or more positive and negative electrodes are disposed in a void defined by the flexible silicon base portion, whereby the proximity of the positive and negative electrodes provides a restrictive channel within which a liquid can flow along the surface;

a single piece of a cable fused to the electrolyte sensor through a strain relief.

* * * * *